United States Patent [19]
Smith

[11] Patent Number: 5,601,595
[45] Date of Patent: Feb. 11, 1997

[54] REMOBABLE THROMBUS FILTER

[75] Inventor: Scott R. Smith, Chaska, Minn.

[73] Assignee: SciMed Life Systems, Inc., Maple Grove, Minn.

[21] Appl. No.: 328,629

[22] Filed: Oct. 25, 1994

[51] Int. Cl.$^6$ .................................................. A61B 17/00
[52] U.S. Cl. .......................................................... 606/200
[58] Field of Search ................................... 606/200, 198, 606/191; 604/104, –108

[56] References Cited

U.S. PATENT DOCUMENTS

| | | |
|---|---|---|
| 3,334,629 | 8/1967 | Cohn . |
| 3,467,102 | 9/1969 | Fogarty et al. . |
| 3,540,431 | 11/1970 | Mobin-Uddin . |
| 3,868,956 | 3/1975 | Alfidi et al. . |
| 3,952,747 | 4/1976 | Kimmell, Jr. . |
| 4,425,908 | 1/1984 | Simon . |
| 4,430,081 | 2/1984 | Timmermans ..................... 604/256 |
| 4,494,531 | 1/1985 | Gianturco . |
| 4,619,246 | 10/1986 | Molgaard-Nielsen et al. . |
| 4,643,184 | 2/1987 | Mobin-Uddin . |

(List continued on next page.)

FOREIGN PATENT DOCUMENTS

| | | |
|---|---|---|
| 0117940A2 | 9/1984 | European Pat. Off. . |
| 0270432B1 | 6/1988 | European Pat. Off. . |
| 0293605A1 | 12/1988 | European Pat. Off. . |
| 0350043B1 | 1/1990 | European Pat. Off. . |
| 0430848 | 11/1990 | European Pat. Off. ............. 606/200 |
| 0472334A1 | 2/1992 | European Pat. Off. . |
| 2573646A1 | 11/1984 | France . |
| 2570288 | 3/1986 | France . |
| 2573646 | 5/1986 | France . |
| 2580504 | 10/1986 | France . |
| WO92/03097 | 3/1992 | WIPO . |
| 9312723 | 7/1993 | WIPO ................................. 606/200 |

OTHER PUBLICATIONS

A. M. Palestrant, M. Prince, M. Simon, "Comparative In Vitro Evaluation of the Nitinol Inferior Vena Cava Filter," pp. 351–355, 1982, *Radiology*, 145.

M. Simon, A. M. Palestrant, "Transvenous Devices for the Management of Pulmonary Embolism," pp. 308–318, *CardioVascular and Interventional Radiology*, 3.

A. M. Fadali, S. R. Topaz, M. M. Ameli, V. I. Gott, "A Filtering Device for the Prevention of Particulate Embolization During the Course of Cardiac Surgery," pp. 634–639, 1968, *Surgery*, 64.

A. Cragg, G. Lund, E. Salomonowitz, J. Rysavy, F. Castaneda, W. Castaneda–Zuniga, K. Amplatz, "A New Percutaneous Vena Cava Filter," pp. 601–604, 1983, *AJR*, 141.

Castaneda–Zuniga et al., "Seminars in Interventional Radiology," pp. 175–241, 1986, *Thieme Medical Publishers, Inc.*, 3.

(List continued on next page.)

*Primary Examiner*—Michael Powell Buiz
*Assistant Examiner*—Patrick W. Rasche
*Attorney, Agent, or Firm*—Nawrocki, Rooney & Sivertson

[57] ABSTRACT

A thrombus filter configured for placement within a blood vessel lumen. The filter having a longitudinal axis. The filter includes first and second units, each unit including a plurality of elongated struts. Each strut has a joining end where the respective struts of each unit are joined together. Each strut also has a free end opposite the joining end. The struts have at least two curves such that in a longitudinal planar projection of the filter, each strut has a first direction of curvature proximate the joining end and an opposite direction of curvature closer to the free end. In a transverse planar projection of the filter, the strut has a first direction of curvature proximate the joining and an opposite direction of curvature closer to the free end. The units can be coupled together in opposition such that the free ends of the struts of the first unit are generally oriented in a first longitudinal direction and the free ends of the struts of the second unit are generally oriented in the opposite longitudinal direction.

15 Claims, 7 Drawing Sheets

U.S. PATENT DOCUMENTS

| | | |
|---|---|---|
| 4,650,466 | 3/1987 | Luther . |
| 4,662,885 | 5/1987 | DiPisa, Jr. . |
| 4,688,553 | 8/1987 | Metals . |
| 4,727,873 | 3/1988 | Mobin-Uddin . |
| 4,781,177 | 11/1988 | Lebigot . |
| 4,793,348 | 12/1988 | Palmaz . |
| 4,817,600 | 4/1989 | Herms et al. . |
| 4,832,055 | 5/1989 | Palestrant . |
| 4,873,978 | 10/1989 | Ginsburg . |
| 4,957,501 | 9/1990 | Lahille et al. . |
| 4,969,891 | 11/1990 | Gewertz . |
| 4,990,156 | 2/1991 | Lefebvre ................................ 606/200 |
| 4,998,539 | 3/1991 | Delsanti . |
| 5,035,706 | 7/1991 | Giantureo et al. . |
| 5,059,205 | 10/1991 | El-Nounou et al. . |
| 5,071,407 | 12/1991 | Termin et al. ........................... 604/104 |
| 5,108,418 | 4/1992 | Lefebvre ................................ 606/200 |
| 5,108,419 | 4/1992 | Reger et al. ............................ 606/200 |
| 5,133,733 | 7/1992 | Rasmussen et al. .................... 606/200 |
| 5,147,379 | 9/1992 | Sabbaghian et al. ............... 606/200 X |
| 5,152,777 | 10/1992 | Goldberg et al. ........................ 606/200 |
| 5,160,342 | 11/1992 | Reger et al. ............................. 606/200 |
| 5,234,458 | 8/1993 | Metals ..................................... 606/200 |
| 5,242,462 | 9/1993 | El-Nounou et al. .................... 606/200 |
| 5,324,304 | 6/1994 | Rasmussen ............................. 606/200 |

OTHER PUBLICATIONS

M. J. Wallace, K. Ogawa, K. Wright, C. H. Carrasco, W. Richi, C. Charnasgavej, "Inferior Vena Caval Stent Filter," pp. 1247–1250, 1986, *AJR*, 147.

M. H. Awh, F. C. Taylor and Chien–Tai Lu, "Spontaneous Fracture of a Vena–Tech Inferior Vena Caval Filter", pp. 177–178, 1991, *AJR*, 157.

G. Lund, J. Rysavy, D. W. Hunter, W. R. Castaneda–Zuniga, L. Amplatz, "Retrievable Vena Caval Filter Percutaneously Introduced", pp. 831, 1985 *Radiology*, 155.

C. J. Grassi, "Inferior Vena Caval Filters: Analysis of Five Currently Available Devices," pp. 813–821, 1991, *AJR*, 156.

G. S. Dorfman, "Percutaneous Inferior Vena Caval Filters," pp. 987–991, 1990 *Radiology*, 174.

R. W. Gunther, H. Schild, A. Fries, and S. Storkel, "Vena Caval Filter to Prevent Pulmonary Embolism: Experimental Study," pp. 315–320, 1985 *Radiology*, 156.

G. Lund, J. Rysavy, E. Solomonowitz et al., "A New Vena Caval Filter for Percutaneous Placement and retrieval: Experimental Study," pp. 369–372, 1984, *Radiology*, 152.

J. J. Alexander, B. L. Gewertz, Chien–Tai Lu and C. K. Zarins, "New Criteria for Placement of a Prophylactic Vena Cava Filter," pp. 405–409, 1986, *Surgery Gynecology & Obstetrics*, 163.

P. J. Golueke, W. V. Garrett, J. E., Thompson et al., "Interruption of the Vena Cava by Means of the Greenfield Filter: Expanding the Indications," pp. 111–117. 1988, *Surgery*, 103.

M. D. Darcy, T. P. Smith, D. W. Hunter et al., "Short–Term Prophylaxis of Pulmonary Emvolism by Using a Retrievable Vena Cava Filter," pp. 836–838, 1986, *AJR*, 147.

D. Kim, D. H. Porter, J. B. Siegel & M. Simon, "Perforation of the Inferior Vena Cava with Aortic and Vertebral Penetration by a Superarenal Greenfield Filter," pp. 721–723, 1989, *Radiology*, 172.

T. Irie, S. Furui, T. Yamauchi, K. Makita, S. Sawada, E. Takenaka, "Relocatable Gianturco Expandable Metallic Stents," pp. 575–577, 1991, *Radiology*, 178.

Maass, D. et al., *Journal of Cardiovascular Surgery*, "The Helix Filter: A New Vena Caval Filter for the Prevention of Pulmonary Embolism", 1985, pp. 116–117.

REMOBABLE THROMBUS FILTER

BACKGROUND OF THE INVENTION

The present invention pertains to thrombus filters. In particular, the present invention relates to thrombus filters which can be securely affixed at a selected location in the vascular system and removed when no longer required.

In recent years, pulmonary embolism has become an increasingly common medical emergency. Pulmonary embolisms may be caused by venous thrombosis, which in turn may be caused by blood flow retention, venous intima damage or coagulation abnormalities. Emergency or prophylactic treatments for these conditions includes anti-coagulant therapy, thrombolytic therapy, thrombectomy and inferior vena cava blocking procedures.

Among these therapeutic options, when an inferior vena cava blocking procedure is selected, one option is to perform a laparotomy under general anesthesia during which the inferior vena cava is ligated, sutured and shortened, or clipped. A laparotomy however, requires a general anesthetic and is susceptible to thrombosis formation due to the discontinuation of anti-coagulate therapy prior to surgery. Another option is to intravenously insert a thrombus filter into the inferior vena cava which requires a local anesthetic. Percutaneous filter insertion is now widely employed since it requires only a local anesthetic. However, such filters become affixed in the inner vena cava wall by neointimal hyperplasia within two or three weeks after being implanted, after which they cannot be removed percutaneously.

Prior thrombus filters which may be removed percutaneously have included generally linear or column-like struts which tend to transfer forces along the longitudinal axis of the struts. If the vessel is compressed asymmetrically, the filter elongates forcing the struts into the vessel wall which may damage the vessel.

SUMMARY OF THE INVENTION

The present invention pertains to an improved thrombus filter having struts configured to reduce the transmission of force along their longitudinal axes. The filter in accordance with the present invention provides struts which behave more as cantilevered beams than those filters which have struts tending to transfer forces primarily along the struts' longitudinal axes.

In an embodiment of the thrombus filter for placement within a blood vessel lumen, in accordance with the present invention, the filter includes a longitudinal axis. The filter also includes first and second units, each unit including a plurality of elongated struts. Each strut has a joining end where the respective struts of each unit are joined together. Each strut has a free end opposite the joining end. The struts extend generally radially outward from the longitudinal axis of the filter and generally longitudinally.

Each strut has at least two curves such that in a longitudinal planar projection of the filter each strut has a first direction of curvature proximate the joining end and an opposite direction of curvature closer to the free end. In a transverse planar projection of the filter, each strut has a first direction of curvature proximate the joining end and an opposite direction of curvature closer to the free end.

The first and second units are coupled together in opposition such that the free ends of the struts of the first unit are generally oriented in a first longitudinal direction and the free ends of the struts of the second unit are generally oriented in the opposite longitudinal direction. Several couplings are available to releasably couple the first and second units together.

The free ends of the struts can include a sharpened anchoring tip and an adjacent flexible pad. The filter may also include a stream lining sheath covering the struts proximate the joining ends to reduce intraluminal blood flow turbulence.

DETAILED DESCRIPTION OF DRAWINGS

Figure 1:
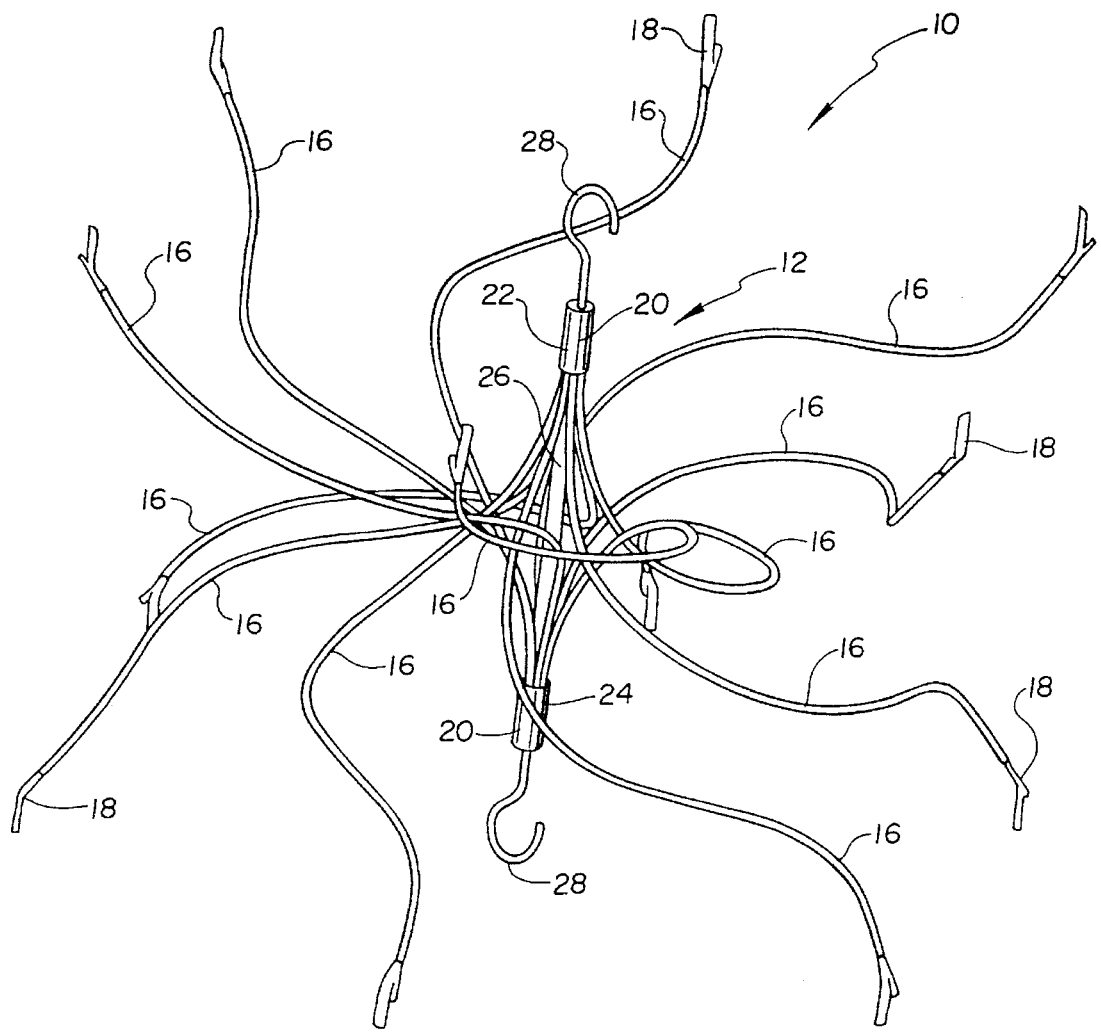
FIG. 1 is perspective view of a filter in accordance with the present invention.

Referring now to the drawings wherein like reference numerals refer to like elements throughout the several views, FIG. 1 shows a perspective view of a thrombus filter in accordance with the present invention and generally referred to by the numeral 10. Thrombus filter 10 includes first and second units 12 and 14, respectively. Each unit 12 and 14 includes a plurality of struts 16. Each strut includes a free end 18 and a joining end 20. Free ends 18 include a sharpened portion 19 and an adjacent flexible pad portion 21. The joining ends 20 of struts 16 of first unit 12 are joined at a hub 22 and the joining ends 20 of the respective struts 16 of second unit 14 are joined at a hub 24. Hubs 22 and 24 are generally aligned along the longitudinal axis of the filter and are fastened together by coupling 26.

Struts 16 of first unit 12 generally radiate from hub 22 away from the longitudinal axis of filter 10 and longitudinally in a direction toward hub 24 of second unit 14. Similarly, struts 16 of second unit 14 generally radiates from hub 24 away from the longitudinal axis of filter 10 and generally longitudinally toward hub 22 of first unit 12. Thus, first unit 12 is coupled in opposition to second unit 14 such that free ends 18 of struts 16 of first unit 12 are generally oriented in the opposite direction from free ends 18 of struts 16 of second unit 14.

Filter 10 also preferably includes two oppositely disposed hooks 28. One hook 28 is attached to hub 22 of first unit 12 and generally extend longitudinally in the opposite direction as struts 16 of first unit 12. Likewise, hook 28 of second unit 14 is connected to and extends from hub 24 and generally longitudinally in the opposite direction as struts 16 extends from hub 24.

Filter 10 may be compressed elastically in a transversed direction and placed in a sheath or catheter lumen. After compression, filter 10 may be delivered to a deployment cite within a vessel lumen by percutaneous catheterization. Within the catheter, the longitudinal axis of filter 10 is generally aligned with, or approximately parallel to the longitudinal axis of the vessel lumen. When the distal end of the catheter reaches the deployment site within the vessel lumen, compressed filter 10 is released from the sheath or catheter where it expands transversely until the free ends 18 of strut 16 reach the side wall of the vessel lumen.

To allow filter 10 to undergo transverse elastic compression, struts 16 are preferably formed from nitinol wire. Other shaped memory alloy wires and super elastic metal wires may be used as well as stainless steel, tungsten, platinum, and chromium alloy wires. In a preferred embodiment, struts 16 are formed from 0.011 inch diameter nitinol wire having a portion proximate free ends 18 having a diameter of 0.015 to improve visibility and strength, and a portion proximate joining end 20 having a diameter of between 0.012 to 0.015 inch to improve strength and fatigue performance at the hubs 22 and 24. It can be appreciated that the diameter of the wire can be varied according to the type of wire used and the particular configuration of filter 10. The wires can be formed by heat setting within a rigid mold as well as by other methods known in the art.

Struts 16, in accordance with the present invention have been configured to respond more like cantilevered beams than as columns. That is, significant bending and torsional forces are distributed along struts 16, rather than forces being primarily transmitted along the longitudinal axes of struts 16. By configuring struts 16 to act more as cantilevered beams rather than as columns, it is believed that the struts will act more independently. By acting independently, struts 16 transmit less force to hubs 22 and 24 and other struts 16, especially those forces tending to rotate filter 10 transversely within a vessel lumen.

Several criteria are taken into account in the design of struts 16. Each strut 16 should be configured and formed of material which enables struts 16 to be collapsed for delivery to a deployment location within a vessel lumen. Struts 16, however, should not produce transverse or longitudinal forces which are so great that free ends 18 of struts 16 damage the vessel wall. Upon deployment of filter 10, struts 16 should be spaced closely enough to intercept thrombus within the range of about 3.0 millimeters to 3.0 centimeters in length, yet not obstruct the vessel so much that excess turbulence is created. Excess turbulence can lead to the formation of additional thrombus. To allow percutaneous removable of filter 10, struts 16 should be configured so that they have a minimum of contact with the vessel wall even when the vessel is compressed axially or radially. If struts 16 come in contact with the vessel wall for an extended period of time neointimal hyperplasia can grow over struts 16, embedding them in the vessel wall. The length and diameter of filter 10 must also be appropriate to the particular application. For example, when deploying filter 10 within the inferior vena cava between the iliac vein and the renal vein, the typical length of the uncompressed filter can be between about 3.0 to 4.0 centimeters in length and about 1.5 to 3.5 centimeters in diameter.

Figure 2:
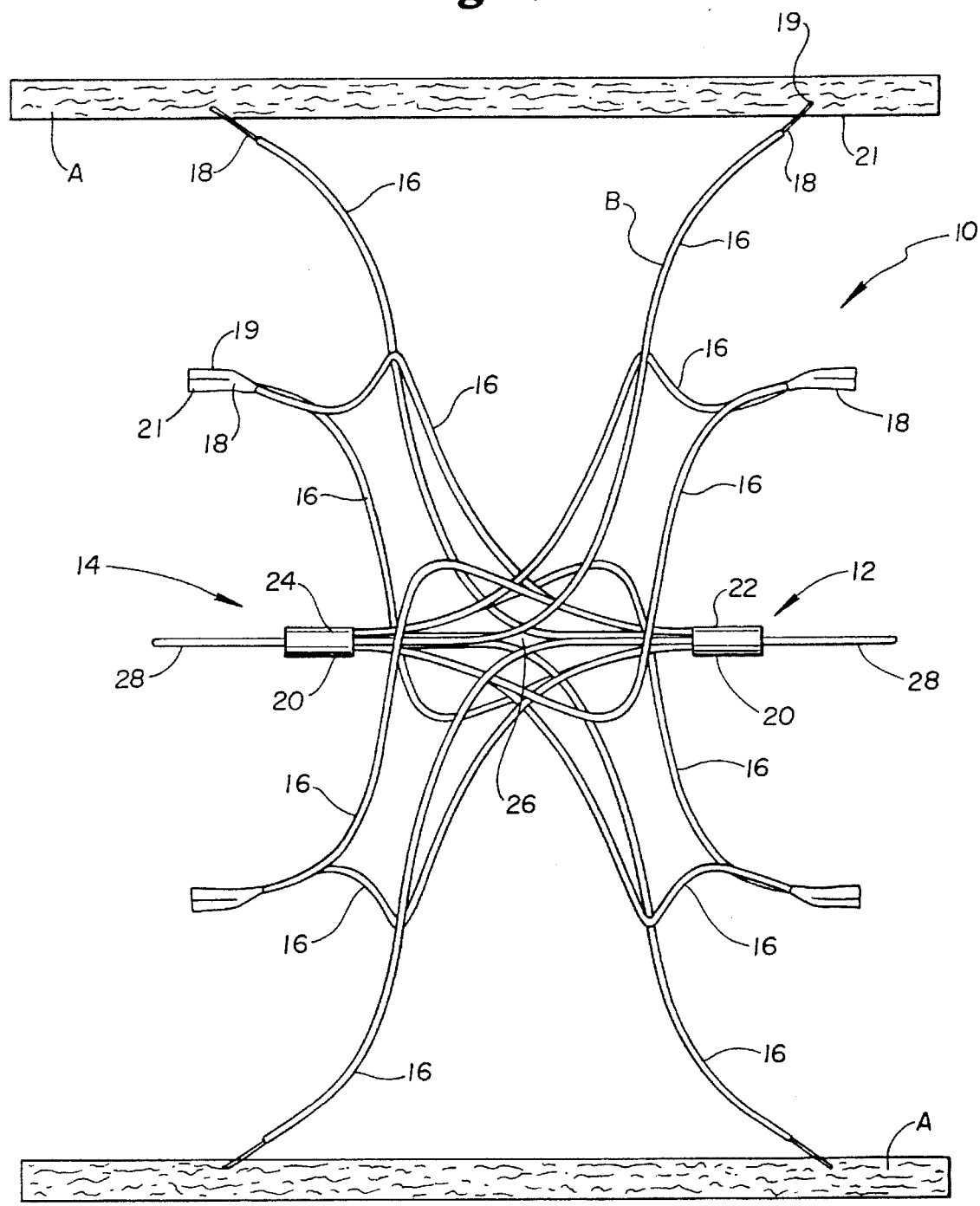
FIG. 2 is side view of the filter in accordance with the present invention.

FIG. 2 shows a side view of a filter 10 deployed within a vessel lumen A. For purposed of describing the shape of strut 16, it is assumed that vessel lumen A is cylindrical and that the longitudinal axis of vessel lumen A is coincident with the longitudinal axis of filter 10. In particular, this view is a longitudinal planar projection of filter 10 within lumen A. As can be seen with particular clarity by reference to the strut 16 labeled with a "B", the strut has at least two curves such that in the longitudinal planar projection of the filter the strut has a first direction of curvature proximate joining end 20 and an opposite direction of curvature closer to free end 18. In particular, the strut 16 referred to by the letter "B" extends from hub 24 generally longitudinally and then curves in a transverse direction away from the longitudinal axis of filter 10. The strut 16 then curves in a longitudinal direction away from hub 24 closer to free end 18 of strut 16. Strut 16 as shown in FIG. 2 begins to immediately curve transversely from hub 24. Strut 16 may, however, first extend longitudinally from hub 24 prior to curving transversely.

In view of the perspective from which struts 16 are viewed in FIG. 2, they appear to have various shapes. Struts 16, as shown in FIG. 2, however, are in fact generally the same shape. For convenience of manufacture, each of the struts may be formed in the same shape, but in accordance with the present invention, they need not so long as the curvature of struts 16 provides the desired performance characteristics.

Preferably, first unit 12 includes six struts 16 and second unit 14 include six struts 16. Fewer of more struts per unit may be used in accordance with the present invention. Varying the number of struts can, however, affect the ability of filter 10 to filter thrombus from the vessel and to retain its position within the vessel.

As shown in FIG. 2, sharpened portions 19 of strut free ends 18 penetrate the wall of vessel lumen A. Further penetration is resisted by pads 21 abutting the vessel wall.

Figure 3:
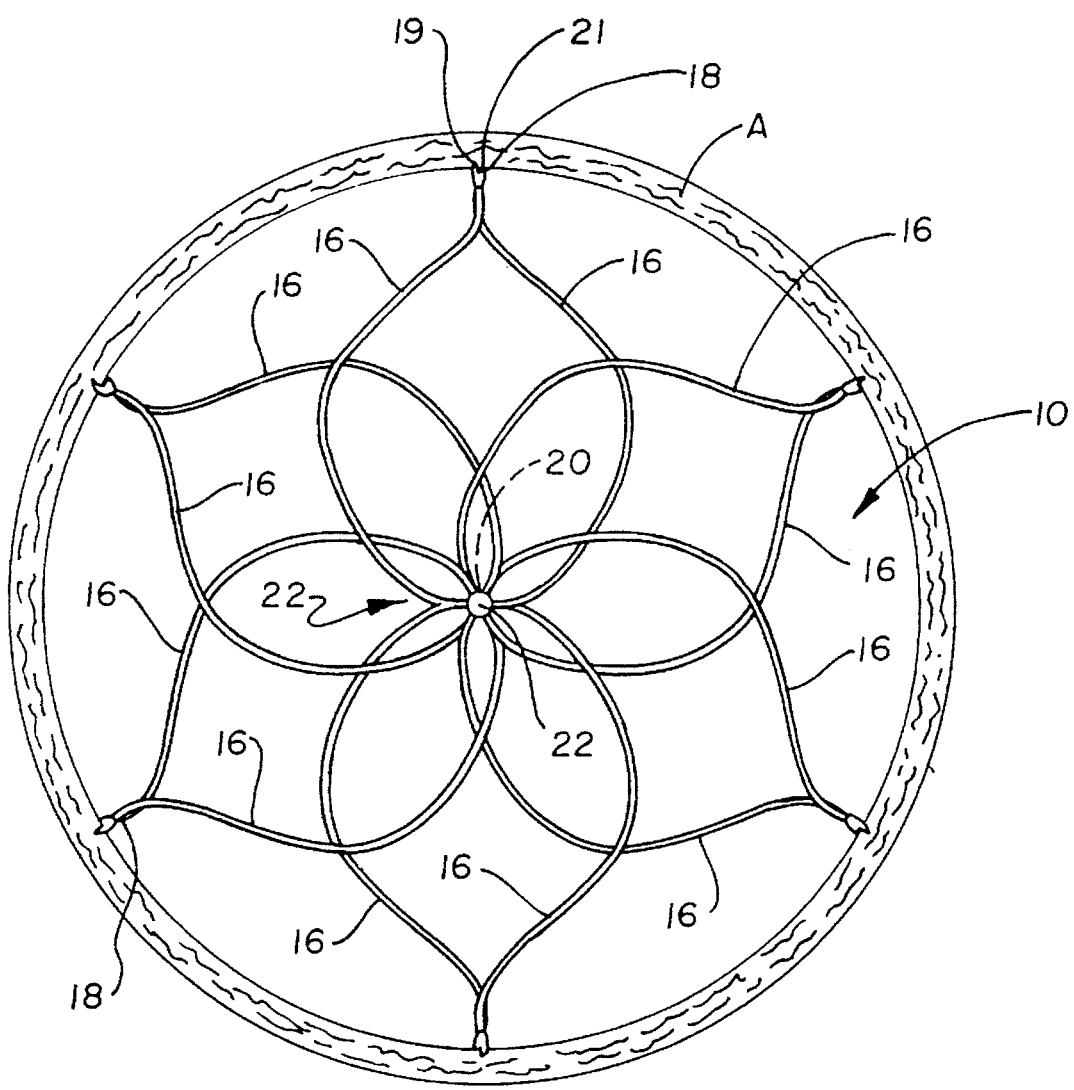
FIG. 3 is an end view of the filter in accordance with the present invention.

FIG. 3 is an end view of filter 10 deployed within the vessel A. Specifically, FIG. 3 shows a transverse planar projection of an end of filter 10. As can be seen, each of the six struts 16 of first and second units 12 and 14, respectively are disposed around the longitudinal axis of filter 10 at approximately even 60 degree intervals. In this view, each strut 16 has a first direction of curvature proximate hubs 22 and 24 respectively and an opposite direction of curvature closer to free ends 18. In particular, each strut 16 extends transversely from the longitudinal axis, then curves in a spiral-like fashion in a first direction (not necessarily the same direction) generally around the longitudinal axis of filter 10. Closer to free ends 18 of struts 16, struts 16 curve in a direction opposite the first direction relative to the longitudinal axis of filter 10.

In view of the complexity of the geometry of each strut 16, the following table is provided to define a typical strut 16 in cylindrical coordinates. Each row in the table defines a point along the center line of strut 16, the point in the first row being at the extreme joining end 20 of strut 16 and point in the last row being at the extreme free end 18 of strut 16. Each of the remaining rows identify intermediate points along a center line of strut 16. It should be appreciated, however, that the strut 16 defined by the tabulated coordinates is representative only and that numerous alternate geometric configurations may be made in accordance with the present invention.

Cylindrical coordinates are an extension of two dimensional polar coordinates to include a third or longitudinal dimension Z. When describing the typical strut 16 in the table, the longitudinal or Z axis of the cylindrical coordinates has been chosen to be coincident with the longitudinal axis of filter 10. In the table, the first column is the radial distance R in inches from the Z axis to the center line of strut 16. The second column is the angular distance θ from a reference line and the third column is linear distance Z perpendicular to a plane including the referenced line. The coordinates in the table assume an initial radial offset of joining end 20 from the longitudinal axis of 0.011 inches.

| R | θ | Z |
|---|---|---|
| 0.011000 | 0.000000° | 0.000000 |
| 0.011000 | 0.000000° | 0.025000 |
| 0.025000 | 0.000000° | 0.100000 |
| 0.025000 | 10.374822° | 0.250000 |
| 0.452243 | 54.969992° | 0.250000 |
| 0.669958 | 90.000000° | 0.553000 |
| 0.730495 | 90.000000° | 0.636188 |

Figure 4:
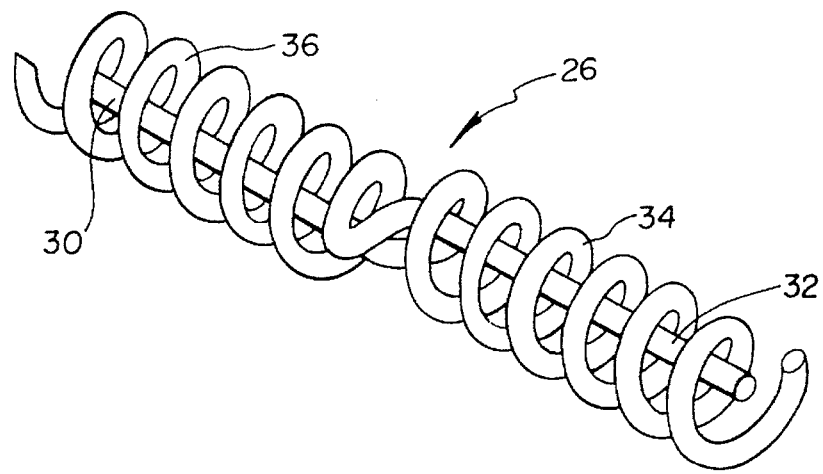
FIG. 4 is a cross sectional view of a coupling for coupling first and second units of the filter together.

FIG. 4 shows a side view of coupling 26. Coupling 26 includes a first wire 30 extending generally longitudinally from hub 24 of second unit 14 toward hub 22 and a second wire 32 extending generally longitudinally from hub 22 of first unit 12 toward hub 24. An end of wire 30 opposite hub 22 is formed into a helix or coil 34. Similarly, an end of wire 32 opposite hub 24 is formed into a coil or helix shape 36. A portion of wire 30 extends through helix 36 and a portion of wire 32 extends through helix 34 to couple wires 30 to wire 32 and consequently first unit 12 to second unit 14 respectively. Coils 34 and 36 must be rigid enough to resist premature uncoupling and flexible enough to uncouple when hooks 28 are pulled in opposite longitudinal directions.

Figure 5:
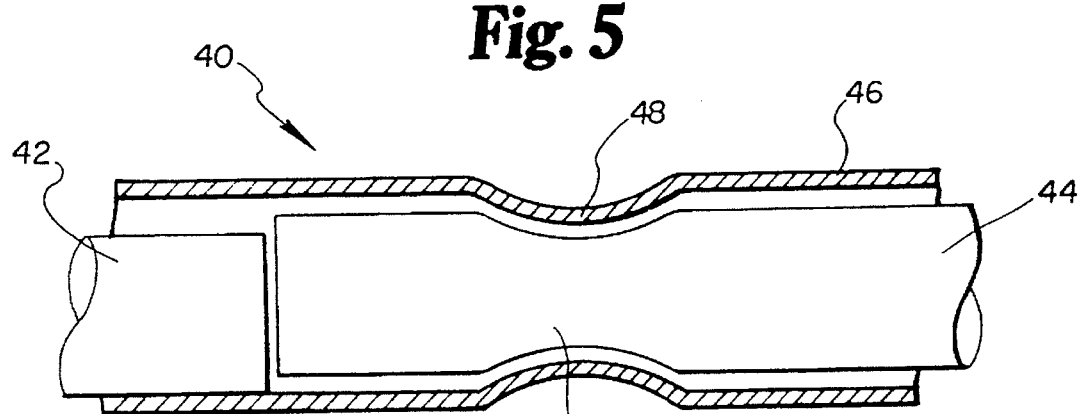
FIG. 5 is a cross sectional view of an alternate embodiment of the coupling for coupling the first and second units of the filter together.

FIG. 5 shows an alternate coupling 40. Coupling 40 includes a first wire 42 extending from hub 22 of first unit 12 like wire 30. Coupling 40 includes a second wire 44 extending from hub 24 of second unit 14 similarly to wire 32. A tube 46 is attached, by adhesive or other suitable means, to an end of wire 42 opposite hub 22. Tube 46 may include a crimp 48 resiliently engageable with a narrowed portion 50 of wire 44. Alternately, tube 46 may include an expanded portion engageable with an expanded end of wire 44. Tube 46 must be rigid enough to prevent premature uncoupling, however, tube 46 must be flexible enough to allow wire 44 to be removed from tube 46 when hooks 28 are pulled in opposite longitudinal directions.

Figure 6:
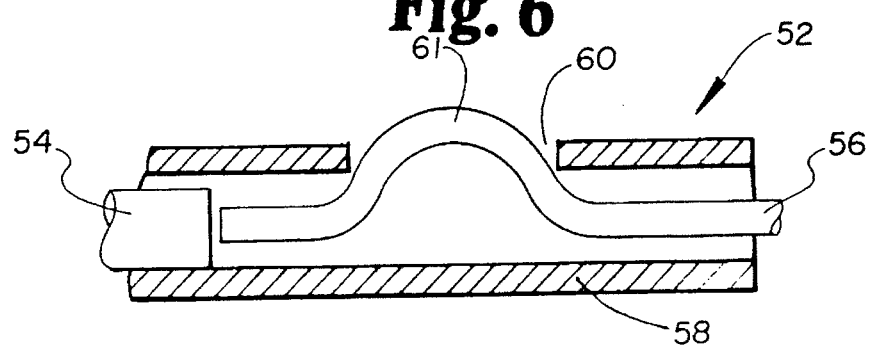
FIG. 6 is cross sectional view of another alternate embodiment of the coupling for coupling the first and second unit of the filter together.

FIG. 6 is a cross sectional view of another alternate coupling 52 taken along the longitudinal axis of the filter. Coupling 52 includes a first wire 54 extending from hub 22 of first unit 12 longitudinally toward hub 24 of second unit 14 and a second wire 56 extending longitudinally from hub 24 of second unit 14 toward hub 22. A tube 58 is attached by adhesive or other suitable means to an end of wire 54 opposite hub 22. A notch 60 extends through a side wall of tube 58. Wire 56 includes a bend 61 which can resiliently engage notch 60 when wire 56 is inserted into tube 58. Coupling 52 may be uncoupled by pulling hooks 28 in an opposite longitudinal direction. Wires 54 and 56 and tube 58 should be sufficiently strong to resist premature uncoupling. They may, for example, be made from stainless steel or a similarly durable material. Wire 56 must be resilient enough to engage notch 60 when wire 56 is inserted into tube 58, but rigid enough that premature uncoupling is avoided.

Figure 7:
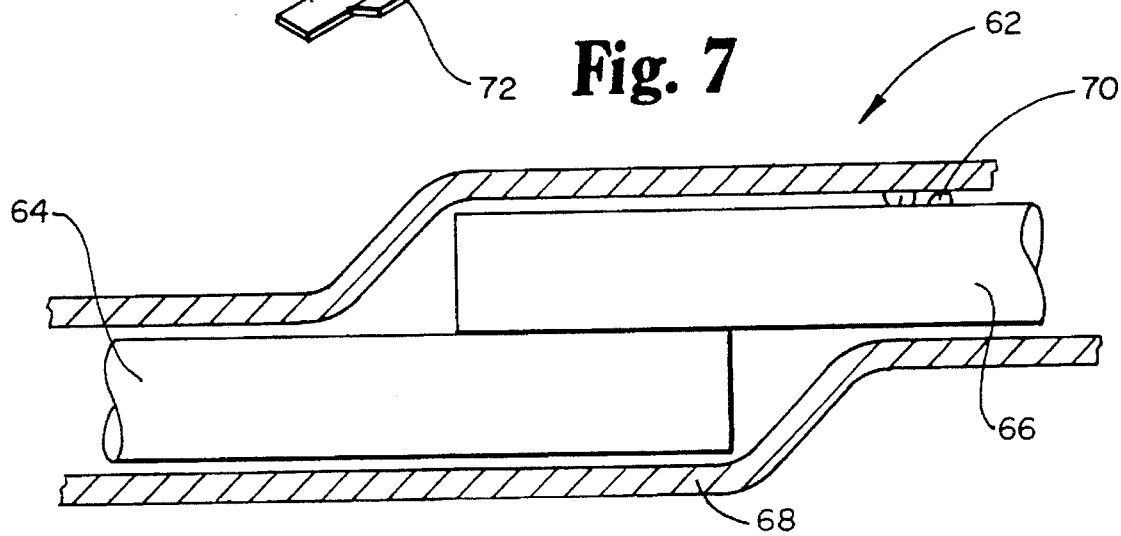
FIG. 7 is a cross sectional view of yet another alternate embodiment of the coupling for coupling the first and second units of the filter together.

FIG. 7 shows still another alternate embodiment of a coupling 62. Coupling 62 includes a first wire 64 extending generally longitudinally from hub 22 of first unit 12 toward hub 24 of second unit 14, and a wire 66 extending from hub 24 generally longitudinally toward hub 22. The end of wire 64 opposite 22 and the end of wire 66 opposite hub 24 overlap and are coupled by a heat shrink wrap 68, such as polytetrafluoroethylene (PTFE). An adhesive 70 bonds heat shrink wrap 68 to wire 66. When hooks 28 of hubs 22 and 24 are pulled in opposite directions, wire 64 is pulled away from wire 66 and shrink wrap 68. Heat wrap 68 remains adhered to wire 66. Shrink wrap 68 must be sufficiently strong and adhesive to prevent premature uncoupling of wires 64 and 66.

Figure 8:
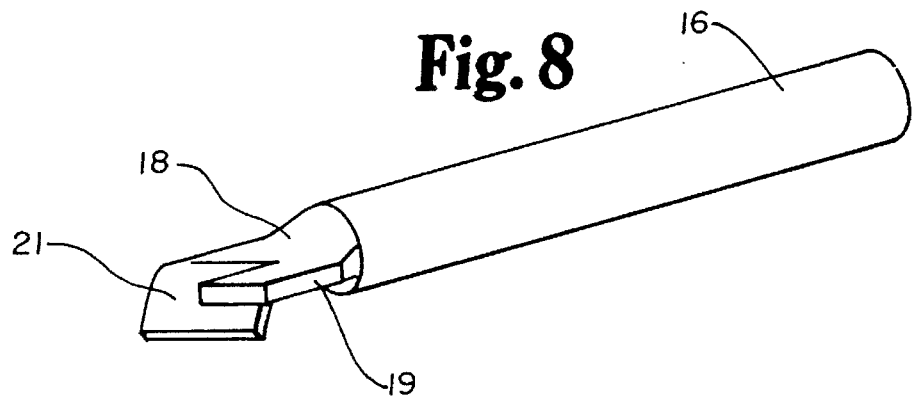
FIG. 8 is perspective view of a free end of a strut of the filter made in accordance with the present invention.

FIG. 8 is a perspective view of free end 18 of strut 16 including sharpened portion 19 and adjacent flexible pad portion 21. Sharpened portion 19 and pad 21 may be formed integrally with strut 16. This may be accomplished, by, for example, flattening free end 18 of strut 16. Flattened free end 18 can be divided by cutting it into two portions. One of the portions can be further cut to form sharpened portion 19 and the other portion bent toward the longitudinal axis of filter 10 to form pad 21. It can be appreciated that other techniques may be used in accordance with the present invention to form integral sharpened portion 19 and pad 21. Further, it should be understood that sharpened portion 19 and pad 21 may be formed separately and subsequently connected to free end 18 of strut 16 by adhesive, welding or other suitable means.

Figure 9:
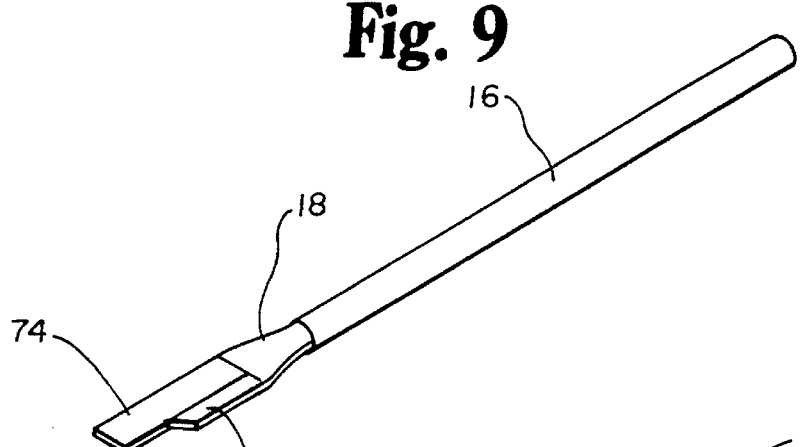
FIG. 9 is a perspective view of an alternate embodiment of the free end of the strut of the filter made in accordance with the present invention.

FIG. 9 shows an alternate embodiment of free end 18 of strut 16 which includes a sharpened portion 72 and pad 74. Sharpened portion 72 and pad 74 can be formed as discussed in the preceding paragraph with respect to sharpened portion 19 and pad 21. Pad 74 is preferably more flexible than sharpened portion 72. This may be accomplished by, for example, flattening pad 74 more than sharpened portion 72. Pad 74 is also preferably longer than sharpened portion 72. When unstressed, pad 74 can lie in the same plane as portion 72.

Figure 10:
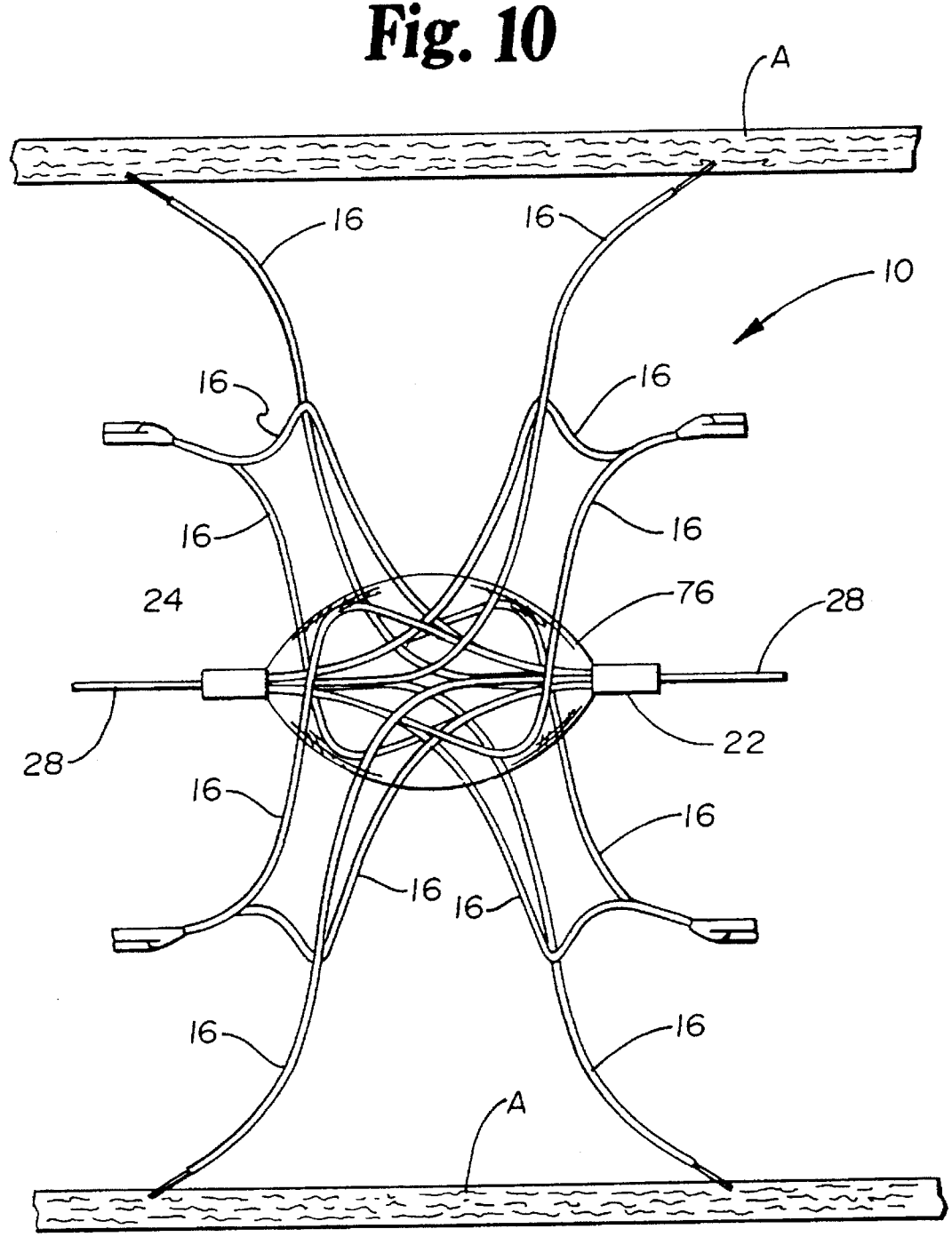
FIG. 10 is side view of an alternate embodiment of the filter in accordance with the present invention including stream lining.

FIG. 10 shows filter 10 including a stream lined encapsulation covering 76 over a portion of struts 16 proximate the longitudinal axis of filter 10. Stream lining of this region of filter 10 is intended to reduce the turbulence near the longitudinal axis of filter 10. The stream lined encapsulation 76 must be formed from a material which is sufficiently durable to survive expansion and contraction of filter 10, yet flexible enough to allow independent flexing of struts 16. Stream line encapsulation 76 may be formed from a heparin loaded collagen, low durometer polyurethane or other similarly suitable material.

Figure 11:
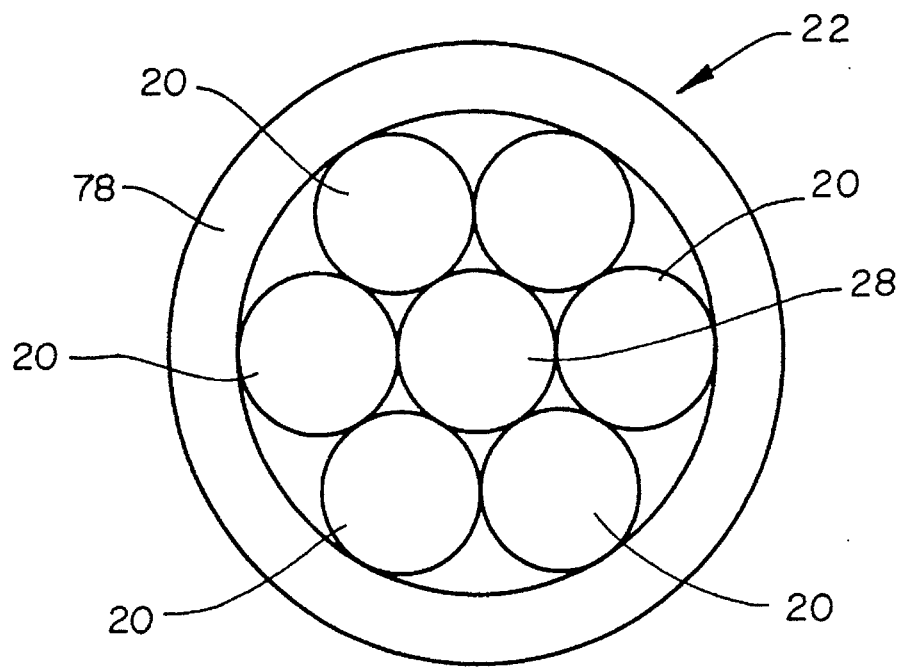
FIG. 11 is a transverse cross sectional view of a hub in accordance with the present invention.

FIG. 11 is a transverse cross sectional view of hub 22, which is essentially similar to hub 24. As shown in FIG. 11, joining ends 20 of struts 16 are arranged around hook 28 within a tube 78. It should be noted that hook 28 may be an integral extension of wire 30 of coupling 26. Wire 32 of coupling 26 of hub 24 and the other coupling wires of the alternate coupling embodiments may be similarly integrally formed. If these corresponding wires are not integrally formed an end of each wire can extend into the respective hub to be joined with joining ends 20 like hook 28 shown in FIG. 11. Tube 78 can be a hypotube or other similarly suitable member. Within tube 78 joining ends 20 and hook 28 may be welded together, crimped, diffusion bonded, press fit, swagged or held together by other suitable means.

Figure 12:
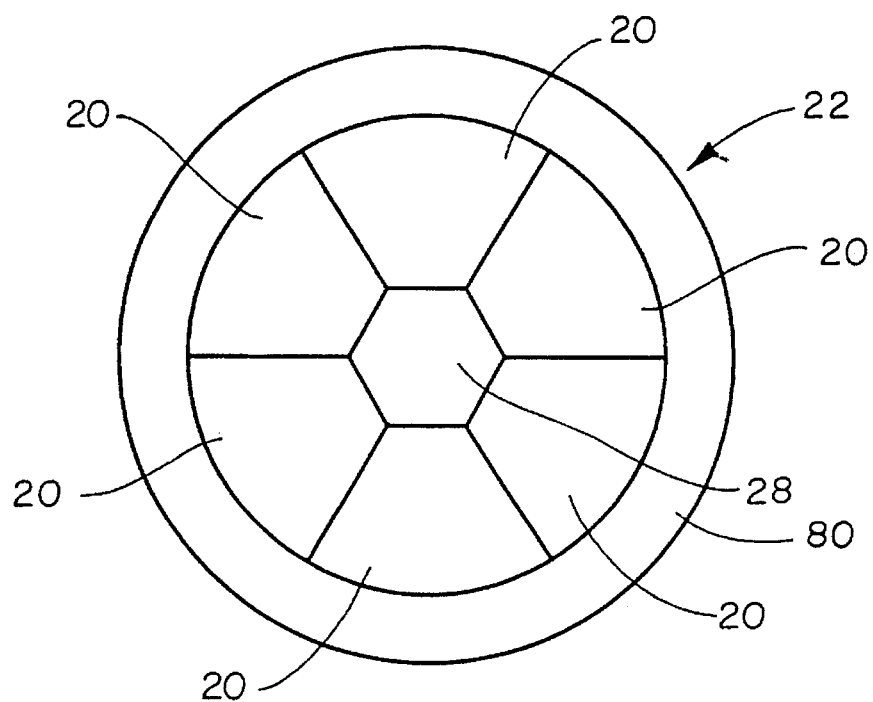
FIG. 12 is a transverse cross sectional view of an alternate hub in accordance with the present invention.

FIG. 12 is a transverse cross sectional view of an alternate embodiment of hub 22 including a tubular member 80 which has been compressed around joining ends 20 of strut 16 and hook 28. Compression of tube 80 causes a deformation of the circular cross sections of ends 20 and hook 28 to form an abutting planar sides between ends 20 and hook 28. Like the embodiment of hub 22 described in the previous paragraph, the respective hooks and wires may be formed integrally or separately and attached to hub 22 accordingly. Any of the joining methods mentioned above such as welding may be used in addition to compressing tube 80.

In use, it is important to measure the inside diameter of the patient's vessel so that a filter having the appropriate diameter is selected. If a filter is undersized there is a risk that it could migrate within the vessel lumen. If filter 10 is oversized it may put undue stress on the vessel wall. A filter having an unstressed diameter equal to approximately 1.3 times the diameter of the vessel into which it is planted has been found to be desirable. This ratio is exemplary only, it being understood that the actual ratio will depend on the particular configuration of struts 16 and the material used to form them.

The thrombus filter can be delivered to a deployment site within a vessel lumen by compressing the filter into a sheath or a catheter lumen. The distal end of the catheter is manipulated to a location within the patient's vessel where the filter 10 is to be deployed such that the longitudinal axis of filter 10 is generally coincident or parallel to the longitudinal axis of the vessel. Filter 10 is then urged from the distal end of the catheter lumen into the patient's vessel lumen. Upon release from the catheter lumen, strut 16 expands generally transversely to the longitudinal axis of filter 10 such that sharpened portions 19 penetrate the vessel lumen wall while pads 21 limit the extent of the penetration.

When it becomes necessary or desirable to remove the filter, the following procedure can be followed. Recovery devices can be inserted percutaneously and threaded through endovenous routes to opposite ends of filter 10. The devices must include means for attaching to hooks 28, such as clamps, loops, hooks, or similar means. One device is attached to each hook 28 and the devices are withdrawn in opposite directions such that first and second units 12 and 14 are pulled apart and uncoupled from each other. First and second units 12 and 14 respectively are then withdrawn from the body.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A thrombus filter configured for placement within a blood vessel lumen, and having a longitudinal axis, the filter comprising:

first and second units, each unit including a plurality of elongated struts, each strut having a joining end where the respective struts of each unit are joined together, each strut having a free end opposite the joining end, and each strut having at least two curves such that in a longitudinal planar projection of the filter each strut has a first direction of curvature proximate the joining end and an opposite direction of curvature closer to the free end, wherein each strut may be defined by a polar coordinate system having a z axis, an r axis, and an angle theta, wherein the z axis is the longitudinal axis of the filter, the r axis extends in a radial direction, and angle theta is an angular distance from a reference line, and r and theta increase simultaneously along a portion of the strut, and wherein each strut curves in a spiral-like fashion; and the units are coupled together in opposition such that the free ends of the struts of the first unit are generally oriented in a first longitudinal direction and the free ends of the struts of the second unit are generally oriented in the opposite longitudinal direction.

2. A filter in accordance with claim 1, wherein, in a transverse planar projection of the filter, the strut has a first direction or curvature proximate the joining end and an opposite direction of curvature closer to the free end.

3. A filter in accordance with claim 1, wherein the free end of the strut includes a sharp anchoring tip and an adjacent flexible pad.

4. A filter in accordance with claim 1, further comprising a sheath covering the struts proximate the joining ends providing stream lining of the filter to reduce intraluminal blood flow turbulence.

5. A thrombus filter for placement within a blood vessel lumen, having a longitudinal axis, the filter comprising:

first and second units, each including a plurality of elongated struts, each strut having a joining end and a free end, wherein the respective struts of each unit are joined together generally about the longitudinal axis of the filter at the joining ends, wherein each strut may be defined by a polar coordinate system having a z axis, an r axis, and an angle theta, wherein the z axis is the longitudinal axis of the filter, the r axis extends in a radial direction, and angle theta is an angular distance from a reference line, and r and theta increase simultaneously along a portion of the strut, and wherein each strut curves in a spiral-like fashion;

each strut of the first unit having a first portion extending from the joining end in generally the same longitudinal direction and a second portion which then curves in a transverse direction away from the first portion and then curves in a longitudinal direction closer to the free end;

each strut of the second unit having a first portion extending from the joining end in generally the same longitudinal direction and a second portion which then curves in a transverse direction away from the first portion and then curves in a longitudinaal direction closer to the free end; and the first and second units being coupled in opposition such that the free ends of the first unit struts are generally oriented in a first longitudinal direction and the free ends of the second unit struts are oriented generally in the opposite direction.

6. A filter in accordance with claim 5, wherein as each strut extends transversely from the longitudinal axis, the strut curves in a spiral-like fashion in a first direction generally around the longitudinal axis of the filter.

7. A filter in accordance with claim 6, wherein closer to the free end of the struts, the strut curves in a direction opposite the first direction relative to the longitudinal axis of the filter.

8. A filter in accordance with claim 5, wherein the free end of the strut includes a sharp anchoring tip and adjacent flexible pad.

9. A filter in accordance with claim 5, further comprising a sheath covering the struts proximate the joining ends providing streamlining of the filter to reduce intraluminal blood flow turbulence.

10. A thrombus filter for placement within a blood vessel, having a longitudinal axis, the filter comprising:

first and second units, each including a plurality of elongated struts, each strut having a joining end and a free end, wherein the respective struts of each unit are joined together generally about the longitudinal axis of the filter at the joining ends;

each strut of the first unit having a first portion extending from the joining end in generally the same longitudinal direction and then curves in a transverse direction away from the first portion;

each strut of the second unit having a first portion extending from the joining end in generally the same longitudinal direction and then curves in a transverse direction away from the first portion; and the first and second units being coupled in opposition such that the free ends of the first unit struts are generally oriented in a first longitudinal direction and the free ends of the second unit struts are oriented generally in the opposite direction, wherein as each strut extends transversely from the longitudinal axis, the strut curves in a spiral-like fashion in the first direction generally around the longitudinal axis of the filter.

11. A filter in accordance with claim 10, wherein closer to the free end of the struts, the strut curves in a direction opposite the first direction relative to the longitudinal axis of the filter.

12. A thrombus filter for placement within a blood vessel lumen, having a longitudinal axis, the filter comprising:

a plurality of elongated struts, each strut having a joining end and a free end, wherein the respective struts are joined together generally about the longitudinal axis of the filter at the joining ends;

each strut having a first portion extending from the joining end in generally the same longitudinal direction and a second portion which then curves in a transverse direction away from the first portion and then curves in a longitudinal direction closer to the free end, wherein as each strut extends transversely from the longitudinal axis, the strut curves in a spiral-like fashion in a first direction generally around the longitudinal axis of the filter.

13. A filter in accordance with claim 12, wherein closer to the free end of the struts, the strut curves in a direction opposite the first direction relative to the longitudinal axis of the filter.

14. A filter in accordance with claim 12, wherein the free end of the strut includes a sharp anchoring tip and adjacent flexible pad.

15. A filter in accordance with claim 12, further comprising a sheath covering the struts proximate the joining ends providing streamlining of the filter to reduce intraluminal blood flow turbulence.

* * * * *